(12) United States Patent
Nakajima

(10) Patent No.: US 7,733,487 B2
(45) Date of Patent: Jun. 8, 2010

(54) PARTICLE COUNTING METHOD

(75) Inventor: Tsutomu Nakajima, Tokyo (JP)

(73) Assignee: Rion Co., Ltd., Tokyo (JP)

( * ) Notice: Subject to any disclaimer, the term of this patent is extended or adjusted under 35 U.S.C. 154(b) by 274 days.

(21) Appl. No.: 12/062,871

(22) Filed: Apr. 4, 2008

(65) Prior Publication Data

US 2008/0246963 A1 Oct. 9, 2008

(30) Foreign Application Priority Data

Apr. 5, 2007 (JP) ............... 2007-099169
Jun. 12, 2007 (JP) ............... 2007-155109

(51) Int. Cl.
*G01N 15/02* (2006.01)
*G01N 21/00* (2006.01)

(52) U.S. Cl. .............. 356/337; 356/335; 356/336

(58) Field of Classification Search ......... 356/335–344, 356/445–448
See application file for complete search history.

(56) References Cited

U.S. PATENT DOCUMENTS 4,521,521 A * 6/1985 Abbott et al. ............... 436/517
4,701,051 A * 10/1987 Buchhave et al. ........... 356/336
4,830,494 A * 5/1989 Ishikawa et al. ............ 356/336
5,576,827 A * 11/1996 Strickland et al. .......... 356/336
5,870,190 A * 2/1999 Unger ........................ 356/336

FOREIGN PATENT DOCUMENTS

JP 63149541 6/1988
JP 9273987 10/1997

* cited by examiner

Primary Examiner—Gregory J Toatley, Jr.
Assistant Examiner—Jarreas C Underwood
(74) Attorney, Agent, or Firm—Sheridan Ross P.C.

(57) ABSTRACT

A particle counting method is provided whereby a liquid sample is radiated by a laser light, scattered light produced by causing the laser light to hit a particle in the liquid sample is detected by a photoelectric conversion element, and a sample value which is the output of the photoelectric conversion element is sequentially compared to a threshold preset for each particle size range, thereby counting the number of particles for each particle size range, the method comprising: a timer start-up step for starting a timer of a predetermined time when the sample value becomes smaller than a threshold of a minimum particle size for the first time and for sequentially holding the maximum value of the sample value; and a timer extension step for restarting the timer to sequentially hold the maximum value of the sample value when the sample value at the time-out of the timer start-up step is larger than the threshold of the minimum particle size.

4 Claims, 7 Drawing Sheets

PARTICLE COUNTING METHOD

CROSS-REFERENCE TO RELATED APPLICATIONS

This application claims the benefit of priority under 35 U.S.C. §11(e) of Japanese Patent Application Nos. 2007-099169, filed Apr. 5, 2007, and 2007-155109, filed Jun. 12, 2007, the entire disclosures of which are incorporated herein by reference.

BACKGROUND OF THE INVENTION

1. Field of the Invention

The present invention relates to a particle counting method whereby scattered light produced by radiating a fluid sample with a laser light is detected to count the number of particles for each particle size range.

2. Description of the Prior Art

As a conventional method for counting particles in a liquid or in air, a method is known whereby the magnitude of the output voltage of a photoelectric conversion element receiving scattered light caused by particles is analyzed to find the size of particles in a liquid sample, thereby counting the number of particles for each particle size range.

Further, a method is known whereby the number concentration is determined by the time when the output voltage of a photoelectric conversion element receiving scattered light exceeds a predetermined threshold (for example, refer to Patent Document 1). Another method is known whereby the duration time of scattered light is measured to discriminate the scattered light by the particles from a background light (for example, refer to Patent Document 2). A still further method is known whereby a sampled latest value is sequentially compared to a preceding value and, when it is judged that the latest value is smaller than the preceding value, the scope of the particle sizes is searched referring to a particle size table, thereby counting the particles for each particle size range. However, when the pulse width exceeds a predetermined time, the particles are not counted (for example, refer to Patent Document 3).

Patent Document 1: Japanese Patent Application Publication No. H09-273987

Patent Document 2: Japanese Patent Application Publication No. S63-149541

Patent Document 3: Japanese Patent Application Publication No. H11-258145

However, particles moving near an inner wall of a flow cell or particles moving near a flow channel boundary of a flow channel formed as a result of the flow of an air sample are slower than those moving through the center of the flow channel and exhibit unstable behavior. In this manner, there is a problem in that, if a judgment is made only by the time when the output voltage of a photoelectric conversion element exceeds a threshold or by the duration time of scattered light, one particle may be falsely recognized as a plurality of particles or particles may not be counted.

Further, a signal wave form by a large particle is accompanied by an overshoot. In this manner, if a judgment is made only by the time when the output voltage of the photoelectric conversion element exceeds the threshold or by the duration time of the scattered light, there is a problem in that one particle may be falsely recognized as a plurality of particles.

SUMMARY OF THE INVENTION

It is therefore an object of the present invention to solve the problems seen in the prior art and to provide a particle counting method whereby one particle is not recognized as a plurality of particles.

In order to attain this object, according to a first aspect of the present invention, a particle counting method is provided, whereby a fluid sample is radiated by a laser light, scattered light produced by causing the laser light to hit a particle in the fluid sample is detected by a photoelectric conversion element, and a maximum value of the output of the photoelectric conversion element is sequentially compared to a threshold preset for each particle size range, thereby counting the number of particles for each particle size range, wherein the method comprises:

a minimum threshold comparing step for comparing a sample value of the output of the photoelectric conversion element to a threshold of the minimum particle size; a timer start-up step for starting a timer of a predetermined time when the magnitude relation between the sample value and the minimum particle size threshold changes in the minimum threshold comparing step; and a counting step for incrementing by one the number of particles of a particle size range corresponding to the maximum sample value among the sample values collected up until the time that the timer is terminated and the sample value becomes smaller than the minimum particle size threshold.

According to a second aspect of the present invention, a particle counting method is provided, whereby a liquid sample is radiated by a laser light, scattered light produced by causing the laser light to hit a particle in the liquid sample is detected by a photoelectric conversion element, and a maximum value of the output of the photoelectric conversion element is sequentially compared to a threshold preset for each particle size range, thereby counting the number of particles for each particle size range, wherein the method comprises:

a minimum threshold comparing step for comparing a sample value of the output of the photoelectric conversion element to a threshold of the minimum particle size; a particle size value detecting step for sequentially holding the maximum value of the sample value when the sample value becomes larger than the threshold of the minimum particle size for the first time in the minimum threshold comparing step;

a timer start-up step for starting a timer of a predetermined time and continuing to sequentially hold the maximum value of the sample value when the sample value becomes smaller than the threshold of the minimum particle size for the first time in the particle size value detecting step;

a timer extension step for restarting the timer and continuing to sequentially hold the maximum value of the sample value when the sample value at the time-out of the timer start-up step is larger than the threshold of the minimum particle size; and a counting step for incrementing by one the number of particles of a particle size range corresponding to the maximum sample value held in the particle size value detecting step, the timer start-up step, and the timer extension step when the sample value in the case of time-out of the timer start-up step or the timer extension step is smaller than the threshold of the minimum particle size.

According to a third aspect of the present invention, a particle counting method is provided, whereby an air sample is radiated by a laser light, scattered light produced by causing the laser light to hit a particle in the air sample is detected by a photoelectric conversion element, and a maximum value of the output of the photoelectric conversion element is sequentially compared to a threshold preset for each particle size range, thereby counting the number of particles for each particle size range; wherein the method comprises:

a minimum threshold comparing step for comparing a sample value of the output of the photoelectric conversion element to a threshold of the minimum particle size;

a particle size value detecting step for sequentially holding the maximum value of the sample value when the sample value becomes larger than the threshold of the minimum particle size in the minimum threshold comparing step for the first time;

a timer start-up step for starting a timer of a predetermined time and continuing to sequentially hold the maximum value of the sample value when the sample value becomes smaller than the threshold of the minimum particle size for the first time in the particle size value detecting step;

a timer extension step for restarting the timer and continuing to sequentially hold the maximum value of the sample value when the sample value at the time-out of the timer start-up step is larger than the threshold of the minimum particle size; and a counting step for incrementing by one the number of particles of a particle size range corresponding to the maximum sample value held by the particle size value detecting step, the timer start-up step, and the timer extension step when the sample value at the time-out of the timer start-up step or the timer extension step is smaller than the threshold of the minimum particle size.

According to a fourth aspect of the present invention, a particle counting method is provided, whereby an air sample is radiated by a laser light, scattered light produced by causing the laser light to hit a particle in the air sample is detected by a photoelectric conversion element, and a maximum value of the output of the photoelectric conversion element is sequentially compared to a threshold preset for each particle size range, thereby counting the number of particles for each particle size range, wherein the method comprises:

a minimum threshold comparing step for comparing a sample value of the output of the photoelectric conversion element to a threshold of the minimum particle size;

a particle size value detecting step for sequentially holding the maximum value of the sample value when the sample value becomes larger than the threshold of the minimum particle size in the minimum threshold comparing step for the first time;

a timer start-up step for starting a timer of a predetermined time at the same time as the start of the particle size value detecting step;

a particle size value detection extending step for continuing to sequentially hold the maximum value until the sample value again becomes smaller than the threshold of the minimum particle size when the sample value at the time-out of the timer start-up step is larger than the threshold of the minimum particle size, and a counting step for incrementing by one the number of particles of a particle size range corresponding to the maximum sample value held in the particle size value detecting step and the particle size value detection extending step when the sample value at the time-out of the timer start-up step is smaller than the threshold of the minimum particle size or when the sample value in the particle size value detection extending step is smaller than the threshold of the minimum particle size.

BRIEF DESCRIPTION OF THE DRAWINGS

The above and other objects, features and advantages of the present invention will become more apparent from the following description when taken in conjunction with the accompanying drawings.

DETAILED DESCRIPTION OF THE PREFERRED EMBODIMENTS

Figure 1:
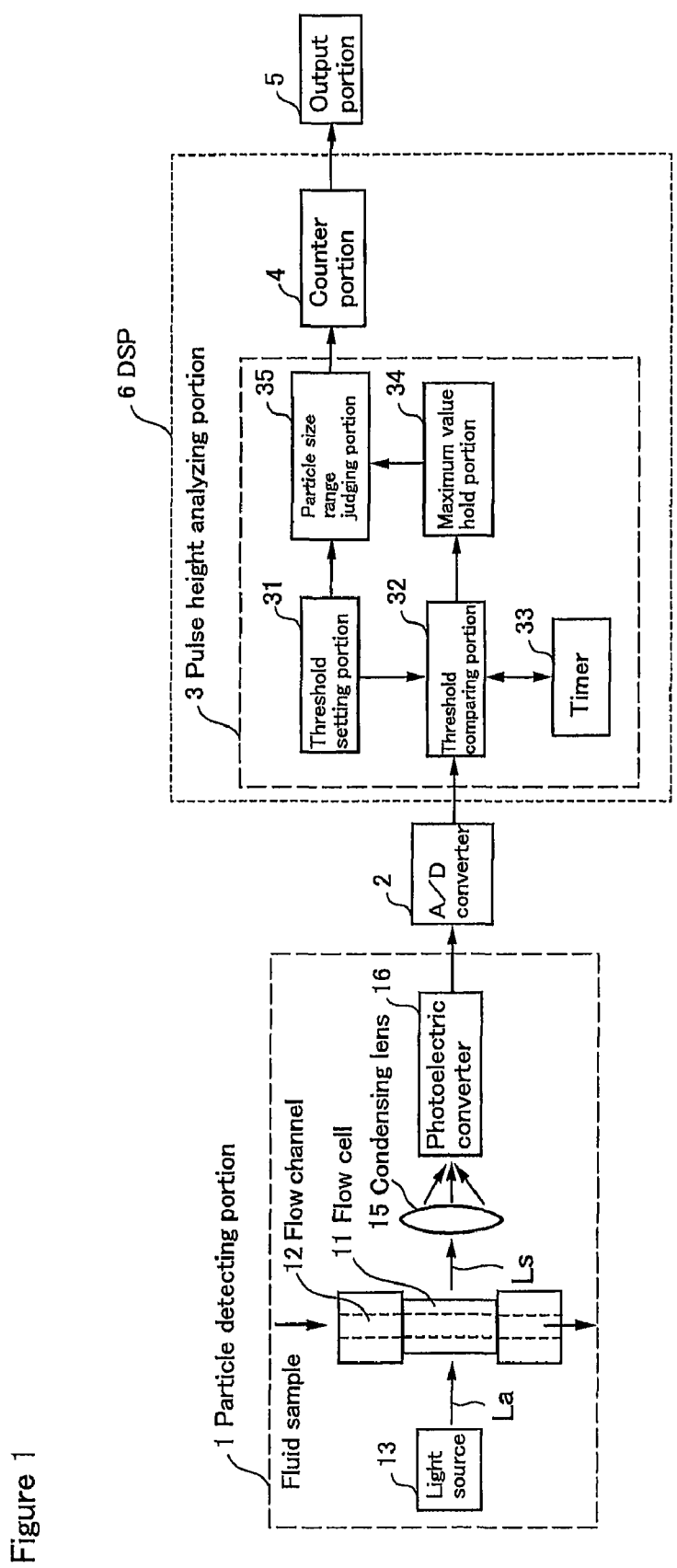
FIG. 1 is a schematic diagram of a counting device using a first embodiment of a particle counting method according to the present invention.
Figure 2:
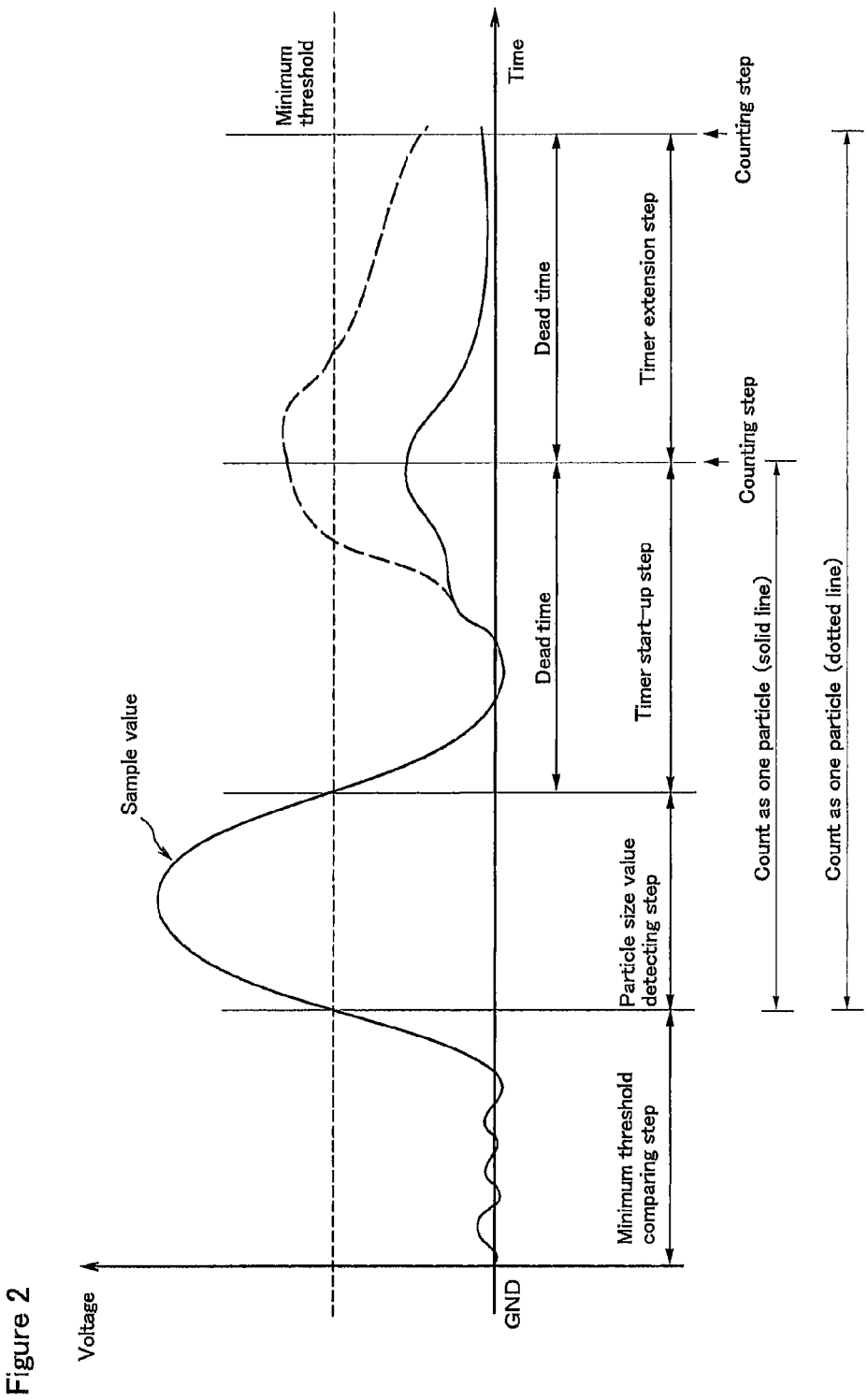
FIG. 2 is an output wave form chart of a photoelectric converter.
Figure 3:
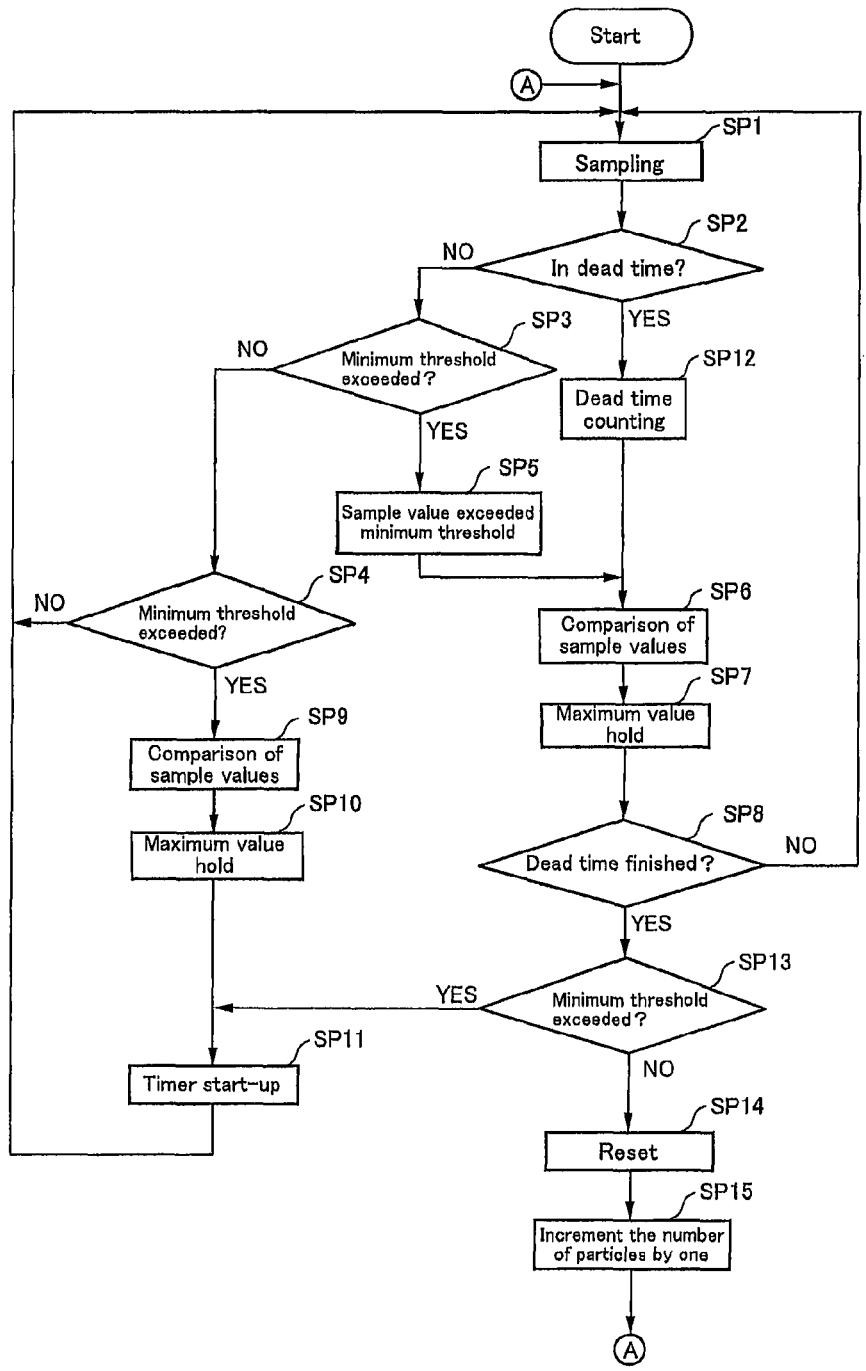
FIG. 3 is a flow chart showing a work procedure.
Figure 4:
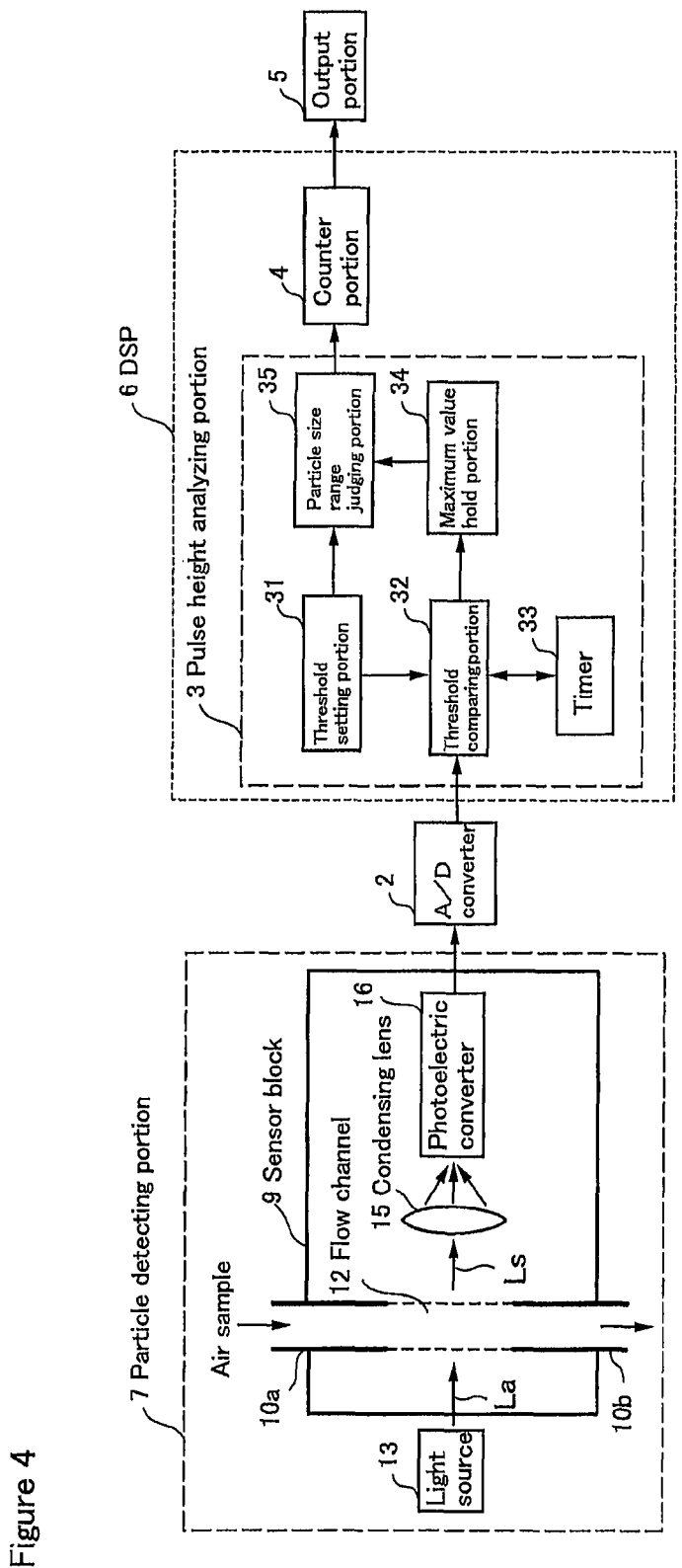
FIG. 4 is a schematic diagram of a counting device using a second embodiment of a particle counting method according to the present invention.
Figure 5:
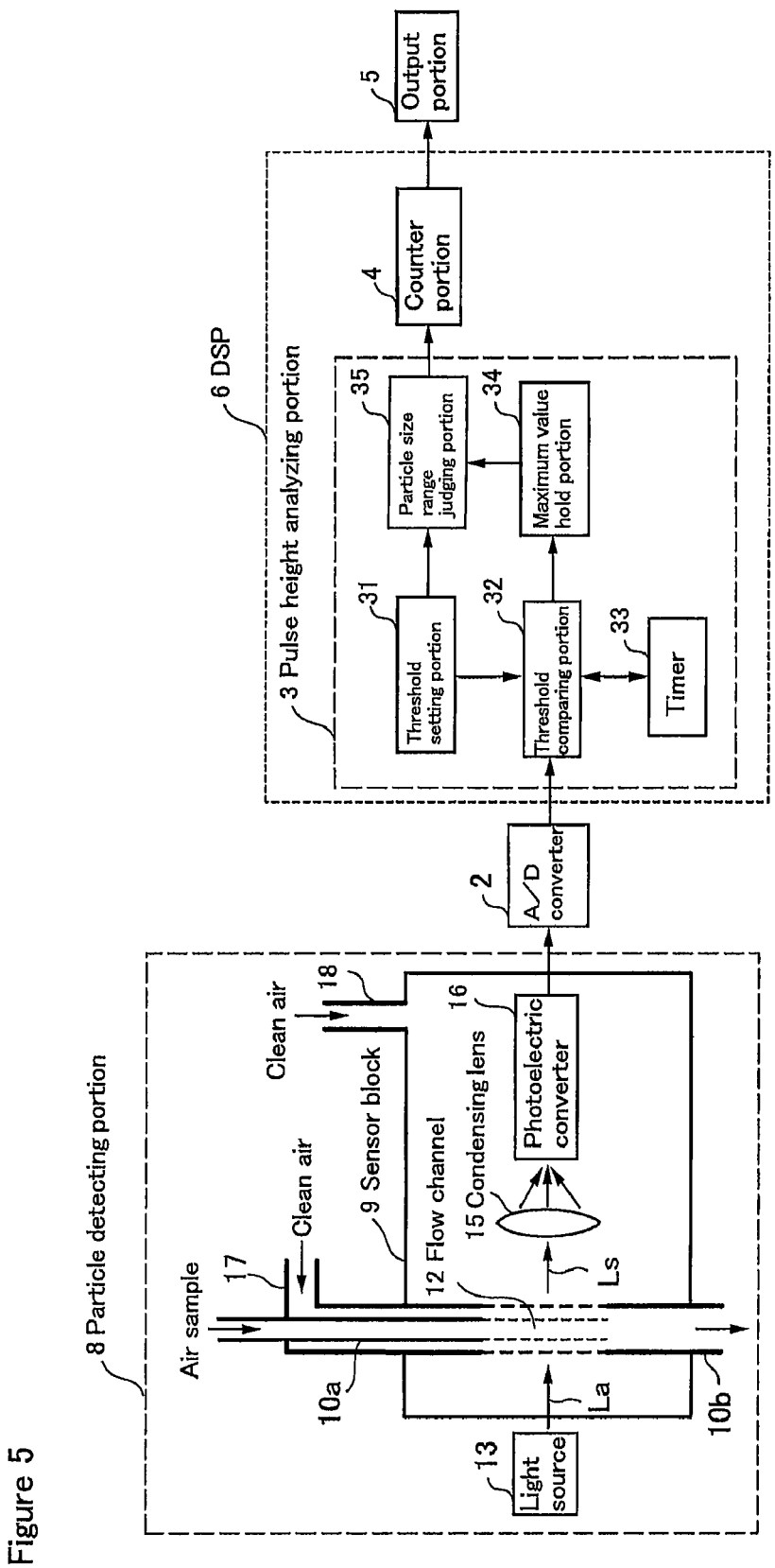
FIG. 5 is a schematic diagram of a counting device using a third embodiment of a particle counting method according to the present invention.
Figure 6:
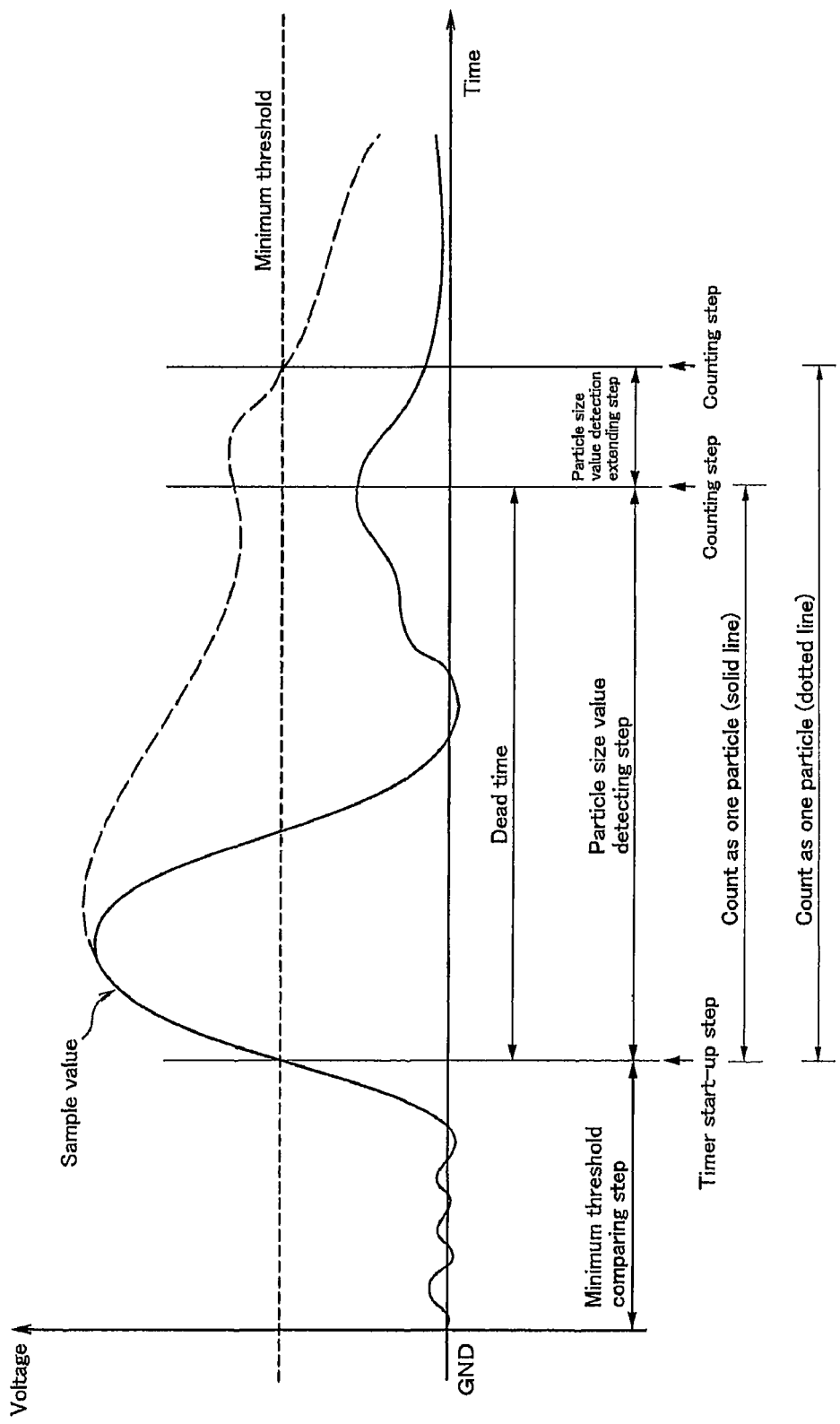
FIG. 6 is an output wave form chart of a photoelectric converter.
Figure 7:
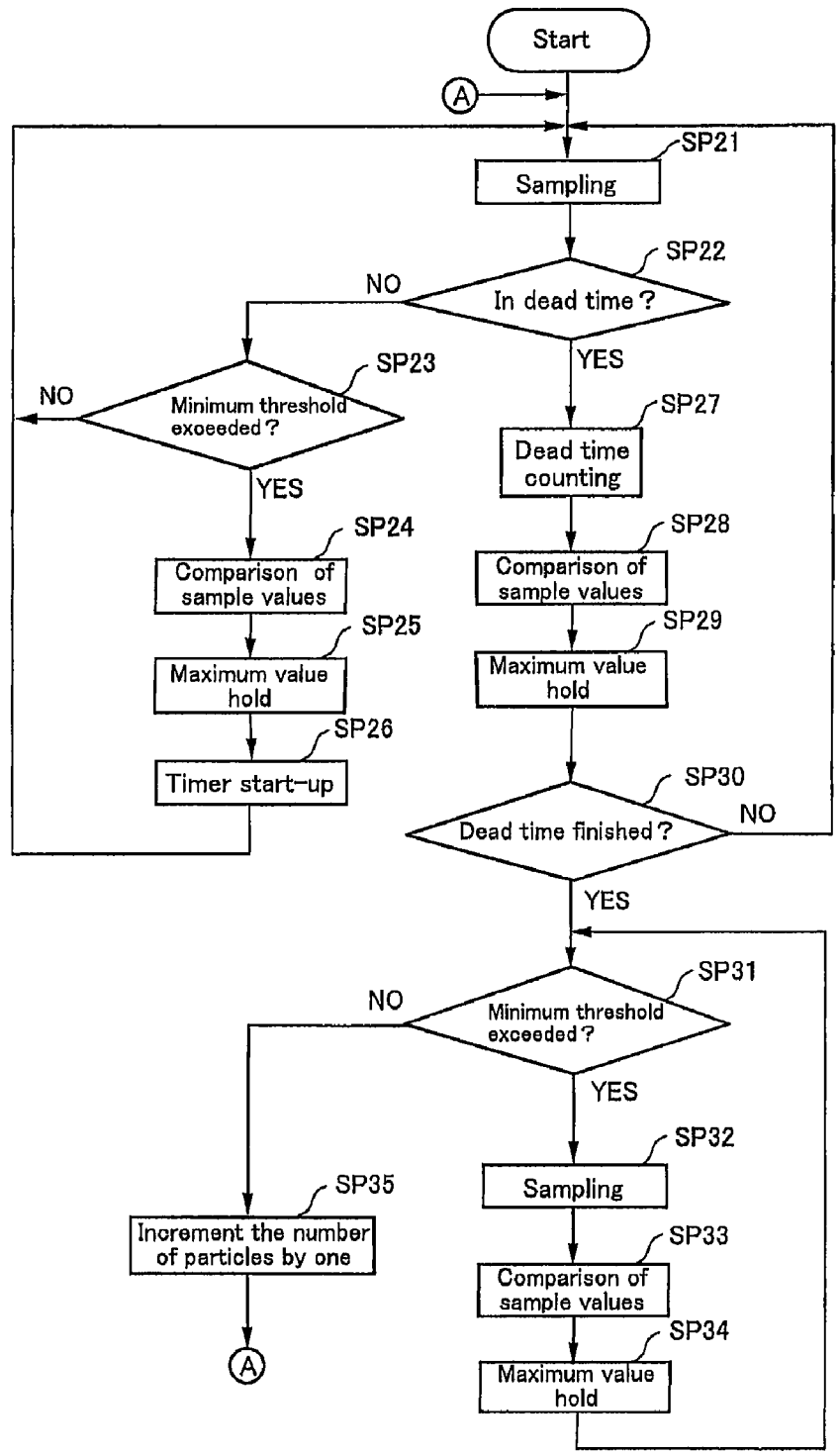
FIG. 7 is a flow chart showing a work procedure.

A preferred embodiment of the present invention will now be described with reference to the accompanying drawings. FIG. 1 is a schematic diagram of a counting device using a first embodiment of a particle counting method according to the present invention. FIG. 2 is an output wave form chart of a photoelectric converter. FIG. 3 is a flow chart showing a work procedure. FIG. 4 is a schematic diagram of a counting device using a second embodiment of a particle counting method according to the present invention. FIG. 5 is a schematic diagram of a counting device using a third embodiment of a particle counting method according to the present invention. FIG. 6 is an output wave form chart of a photoelectric converter. FIG. 7 is a flow chart showing a work procedure.

A counting device using a first embodiment of a particle counting method according to the present invention comprises, as shown in FIG. 1, a particle detecting portion 1 for detecting particles in a fluid sample using a laser light, an A/D converter 2 for converting an output signal of the particle detecting portion 1 to a digital signal, a pulse height analyzing portion 3 for collecting particles from the output signal of the A/D converter 2 for each particle size range (n ranges), a counter portion 4 for receiving the output signal from the pulse height analyzing portion 3 and counting the number of particles for each particle size range (n ranges), and an output portion 5 for outputting the process results of the counter portion 4.

The particle detecting portion 1 comprises a flow channel 12 for introducing a fluid sample formed by a flow cell 11 and the like, a light source 13 for radiating the flow channel 12 with a laser light La to provide a particle detecting area, a condensing lens 15 for condensing a scattered light Ls emitted by the particles passing through the particle detecting area, and a photoelectric converter 16 for converting the light condensed by the condensing lens 15 to a voltage corresponding to the intensity of the light.

The pulse height analyzing portion 3 comprises a threshold setting portion 31 for setting a threshold (n units) corresponding to a particle size range (n ranges) in advance, a threshold comparing portion 32 for comparing a threshold of the threshold setting portion 31 to a sample value obtained by sampling an output signal of the particle detecting portion 1 at a predetermined interval by the A/D converter 2, a timer 33 for proving a dead time to prevent one particle from being counted as two particles, a maximum value hold portion 34 for storing the maximum value of the sample value and comparing the holding maximum value to a new sample value to update the maximum value to a larger value, thereby outputting the maximum value holding at the end of the dead time, and a particle size range judging portion 35 for judging a particle size range corresponding to a particle detected by comparing the maximum value to the threshold and outputting a pulse corresponding to the range. It is to be noted that the pulse height analyzing portion 3 and the counter portion 4 can be composed of a DSP (Digital Signal Processor) 6 or a device such as a FPGA (Field Programmable Gate Array) which can process a digital signal.

The first embodiment of a particle counting method according to the present invention used in the counting device as constructed above is now described with reference to an output wave form chart of the photoelectric converter 16 as shown in FIG. 2 and a flow chart of a work procedure as shown in FIG. 3. In the initial condition, a minimum threshold is held in the maximum value hold portion 34, a dead time is not commenced, and the recorded last sample value is smaller than the minimum threshold. First, in a step SP1, a sample value is set by sampling the output signal of the A/D converter 2 at a predetermined interval (for example, 200 kHz). Then, in a step SP2, it is judged whether the sample value is in the dead time (for example, 200 μsec) or not. If it is judged that the sample value is not in the dead time, a program proceeds to a step SP3, while if it is judged that the sample value is in the dead time, the program proceeds to a step SP12.

In the step SP3, the sample value is first compared to the minimum threshold stored in the threshold setting portion 31 in the threshold comparing portion 32. If the sample value has not exceeded the minimum threshold, the program proceeds to a step SP4, while if the sample value has exceeded the minimum threshold, the program proceeds to a step SP5. In the step SP4, it is judged whether the last sample value has exceeded the minimum threshold. If the last sample value has not exceeded the minimum threshold, the program returns to the step SP1, while if the last sample value has exceeded the minimum threshold, the program proceeds to a step SP9. Now, a loop of step SP1→step SP2→step SP3→step SP4→step SP1 forms a minimum threshold comparing step. Thus, the minimum threshold comparing step is carried out for a period of time until the sample value exceeds the minimum threshold.

Next, the program returns to the step SP1, wherein, when a sample value is set by sampling the output signal of the A/D converter 2 at a predetermined interval, it is judged that the sample value is not in the dead time in the step SP2. When it is judged that the sample value has exceeded the minimum threshold in the step SP3, this fact is stored in the step SP5. Further, in a step SP6, a latest sample value is compared to the last maximum sample value held in the maximum value hold portion 34, wherein, in a step SP7, if larger, this latest sample value is entered as the maximum sample value in the maximum value hold portion 34.

Next, in a step SP8, it is judged whether the dead time is in a finish time or not. If it is judged that the dead time is not in the finish time, the program returns to the step SP1, while if it is judged that the dead time is in the finish time, the program proceeds to a step SP13. Now, a loop of step SP1→step SP2→step SP3→step SP5→step SP6→step SP7→step SP8→step SP1 forms a particle size value detecting step. Thus, the particle size value detecting step is carried out while the sample value has exceeded the minimum threshold.

The program now returns to the step SP1, wherein if a sample value is set by sampling the output signal of the A/D converter 2 at a predetermined interval, it is judged in the step SP2 that the sample value is not in the dead time. If it is judged in the step SP3 that the sample value has not exceeded the minimum threshold, it is judged in the step SP4 that the last sample value has exceeded the minimum threshold (recorded in the step SP5), then the program proceeds to a step SP9. In the step SP9, a latest sample value is compared to a maximum sample value held in the maximum value hold portion 34 and, in a step SP10, if larger, this sample value is entered as the maximum sample value.

Next, in a step SP11, a timer 33 setting the dead time is started. The program now returns to the step SP1, wherein, if a sample value is set by sampling the output signal of the A/D converter 2 at a predetermined interval, it is judged that the sample value is in the dead time in the step SP2 and, in a step SP12, the dead time is counted. Then, in the step SP6, a latest sample value is compared to the last maximum sample value held in the maximum value hold portion 34 and, in the step SP7, if larger, this sample value is entered as the maximum sample value.

Next, in the step SP8, it is judged whether the dead time is in the finish time or not. If it is judged that the dead time is not in the finish time, the program returns to the step SP1, while if it is judged that the dead time is in the finish time, the program proceeds to a step SP13. Now, a loop of step SP1→step SP2→step SP3→step SP4→step SP9→step SP10→step SP11 and a loop of step SP1→step SP2→step SP12→step SP6→step SP7→step SP8→step SP1 form a timer start-up step. Thus, the timer start-up step is carried out during the time until the dead time reaches the finish time.

Next, in the step SP8, if it is judged that the dead time has reached the finish time, the sample value is compared to a minimum threshold in a step SP13. If it is judged that the sample value has exceeded the minimum threshold at the finish time of the dead time, the program proceeds to the step SP11, wherein the timer 33 setting the dead time is restarted. The program now returns to the step SP1, wherein it is it judged that the sample value is in the dead time in the step SP2 and, in a step SP12, the dead time is counted. Then, in the step SP6, the latest sample value is compared to the last maximum sample value held in the maximum value hold portion 34 and, in the step SP7, if larger, this sample value is entered as the maximum sample value.

Next, in the step SP8, it is judged whether the dead time is in a finish time or not. If it is judged that the dead time has not reached the finish time, the program returns to the step SP1, while if it is judged that the dead time has reached the finish time, the program proceeds to a step SP13. Now, a loop of step SP13→step SP11 and a loop of step SP1→step SP2→step SP12 step SP6→step SP7→step SP8→step SP1 form a timer extension step. Thus, the timer extension step is carried out while the dead time has not reached the finish time. In the case where the sample value has exceeded the minimum threshold at the finish time of the dead time, the timer extension step is repeated until the sample value does not exceed the minimum threshold at the finish time of the dead time.

On the other hand, at the finish time the of the dead time, if it is judged that the sample value has not exceeded the minimum threshold in the step SP13, the program proceeds to a step SP14, wherein the entry (step SP5) indicating that the sample value has exceeded the minimum threshold, and the setting (step SP11) that the sample value is in the dead time, are reset. Next, in a step SP15, a particle size range corresponding to a particle detected in the particle size range judging portion 35 is judged from the maximum sample value held in the process of the particle size value detecting step, the timer start-up step and the timer extension step, and the threshold of each particle size range set in the threshold setting portion 31, whereby a pulse is output to a channel of the corresponding particle size range. In the counter portion 4, the number of particles of the particle size range to which the pulse was sent is incremented by one (counting step). The program now returns to the step SP1 for the next counting operation.

By providing such a minimum threshold comparing step, particle size value detecting step, timer start-up step, timer extension step, and counting step, even particles which move slowly through the center of the flow channel near the inner wall of the flow cell 11 and exhibit unstable behavior are counted as one particle and as a result, measuring accuracy improves. In particular, by providing the timer start-up step and the timer extension step, even the signal wave forms by the large particles accompanied by an overshoot are counted as one particle and as a result, measuring accuracy improves.

Next, a counting device using a second embodiment of a particle counting method according to the present invention comprises, as shown in FIG. 4, a particle detecting portion 7 for detecting a particle in an air sample using a laser light, an A/D converter 2 for converting an output signal from the particle detecting portion 7 to a digital signal, a pulse height analyzing portion 3 for collecting a particle from the output signal of the A/D converter 2 for each particle size range (n ranges), a counting portion 4 for receiving the output signal from the pulse height analyzing portion 3 and counting the number of particles for each particle size range (n ranges), and an output portion 5 for outputting the processed results of the counter portion 4. Since the components with the same reference numerals as those shown in FIG. 4 have the same function as those with the same reference numerals as shown in FIG. 1, further explanation is omitted.

The particle detecting portion 7 comprises a sensor block 9, a suction nozzle 10a for introducing air sample into the sensor block 9, an exhaust nozzle 10b for discharging the introduced air sample, a flow channel 12 formed by the flow of the air sample, a light source 13 for radiating the flow channel 12 with a laser light La to provide a particle detecting area, a condensing lens 15 for condensing a scattered light Ls emitted by particles passing through the particle detecting area, and a photoelectric converter 16 for converting the light condensed by the condensing lens 15 to a voltage corresponding to the intensity of the light. In the case where a sheath air pipe disposed coaxially with the suction nozzle 10a to surround the suction nozzle 10a for introducing clean air and a purge air pipe for supplying clean air into the sensor block 9 are not provided, it is often the case that a turbulent flow, as seen in the liquid, is produced in the air.

Since operation of the second embodiment of a particle counting method according to the present invention which is used by the count device as constructed above is the same as that of the first embodiment of a particle count method according to the present invention described with reference to FIG. 2 (output wave form chart of the photoelectric converter 16) and FIG. 3 (flow chart of a work procedure), further description of the wave form of the photoelectric converter 16 and the work procedure is omitted.

By providing such a minimum threshold comparing step, particle size value detecting step, timer start-up step, timer extension step, and counting step, even particles moving slowly through the flow channel center near a flow channel boundary of the flow channel 12 and exhibiting unstable behavior are counted as one particle and as a result, measuring accuracy improves. In particular, by providing the timer start-up step and the timer extension step, even the signal wave forms by a large particle accompanied by an overshoot are counted as one particle and as a result, measuring accuracy improves.

Next, a counting device using a third embodiment of a particle count method according to the present invention comprises, as shown in FIG. 5, a particle detecting portion 8 for detecting a particle in an air sample using a laser light, an A/D converter 2 for converting an output signal from the particle detecting portion 8 to a digital signal, a pulse height analyzing portion 3 for collecting the particle from the output signal of the A/D converter 2 for each particle size range (n ranges), a counting portion 4 for receiving an output signal from the pulse height analyzing portion 3 to count the number of particles for each particle size range (n ranges), and an output portion 5 for outputting the processed results of the counter portion 4. Since the components with the same reference numerals as those shown in FIG. 5 have the same function as the components with the same reference numerals as shown in FIG. 1, further description is omitted.

The particle detecting portion 8 comprises a sensor block 9, a suction nozzle 10a for introducing an air sample into the sensor block 9, an exhaust nozzle 10b for discharging the introduced air sample, a flow channel 12 formed by the flow of the air sample, a light source 13 for radiating the flow channel 12 with a laser light La to provide a particle detecting area, a condensing lens 15 for condensing scattered light Ls emitted by the particles passing through the particle detecting area, and a photoelectric converter 16 for converting the light condensed by the condensing lens 15 to a voltage corresponding to the intensity of the light. Further, a sheath air pipe 17 disposed coaxially with the suction nozzle 10a to surround the suction nozzle 10a for introducing clean air and a purge air pipe 18 for supplying clean air into the sensor block 9 are provided. By using clean air, it is difficult for a turbulent flow to be produced in the flow channel 12 and for the particles to exist apart from the flow channel 12.

A third embodiment of a particle counting method according to the present invention used in the counting device as constructed above will now be described with reference to a wave form chart of a photoelectric converter 16 as shown in FIG. 6 and a flow chart of a work procedure as shown in FIG. 7. In the initial condition, setting is made in such a manner that a minimum threshold is stored in a maximum value hold portion 34, the dead time is not commenced, and the recorded last sample value is smaller than the minimum threshold. First, in a step SP21, a sample value is set by sampling an output signal from the A/D converter 2 at a predetermined interval (for example, 200 kHz). Next, in a step SP22, it is judged whether the sample value is in a dead time (for example, 100 μsec) or not. If it is judged that the sample value is not in the dead time, the program proceeds to a step SP23, while if it is judged that the sample value is in the dead time, the program proceeds to a step SP27.

In the step SP23, the sample value is first compared to a minimum threshold stored in a threshold setting portion 31 in a threshold comparing portion 32. If the sample value has not exceeded the minimum threshold, the program returns to the step SP21, while if the sample value has exceeded the minimum threshold, the program proceeds to a step SP24. Now, a loop of step SP21→step SP22→step SP23→step SP21 form a minimum threshold comparing step. The minimum threshold comparing step is carried out for a period of until the sample value exceeds the minimum threshold.

Next, the program returns to the step SP21, wherein if a sample value is set by sampling the output signal of the A/D converter 2 at a predetermined interval, it is judged in the step SP22 that the sample value is not in the dead time. Further, in the step SP23, if it is judged that the sample value has exceeded the minimum threshold, the program proceeds to the step SP24. In the step SP24, a latest sample value is compared to the last maximum sample value stored in the maximum value hold portion 34 and, in a step SP25, if larger, this sample value is entered as the maximum sample value in the maximum value hold portion 34.

Next, in a step SP26, a timer 33 setting the dead time is started. Now, a loop of step SP21→step SP22→step SP23→step SP24→step SP25→step SP26→step SP21 form a particle size value detecting step. The timer start-up step is carried out for a period of until the timer 33 setting the dead time ends.

Now, the program returns to the step SP21, wherein if a sample value is set by sampling the output signal of the A/D converter 2 at a predetermined interval, it is judged in the step SP22 that the sample value is in the dead time and, in a step SP27, the dead time is counted. Then, in a step SP28, a latest sample value is compared to the last maximum sample value held in the maximum value hold portion 34 and, in a step SP29, if larger, this sample value is entered as the maximum sample value.

Next, in a step SP30, it is judged whether the dead time is in the finish time or not. If it is judged that the dead time is not in the finish time, the program returns to the step SP21, while if it is judged that the dead time is in the finish time, the program proceeds to a step SP31. A loop of step SP21→step SP22→step SP27→step SP28→step SP29→step SP30→step SP21 forms a particle size detecting step. The particle size detecting step is carried out for a period of until the dead time reaches the finish time.

Next, in the step SP30, if it is judged that the dead time is in the finish time, the sample value is compared to the minimum threshold in the step SP31. If it is judged that the sample value has exceeded the minimum threshold, the program proceeds to a step SP32, wherein a sample value is set by newly sampling the output signal of the A/D converter 2 at a predetermined interval and the program proceeds to a step SP33. In the step SP33, the sample value is compared to the last maximum sample value stored in the maximum value hold portion 34 and, in a step SP34, if larger, this sample value is entered as the maximum sample value. Then, the program returns to the step SP31, wherein the sample value is compared to the minimum threshold. A loop of step SP31→step SP32→step SP33→step SP34→step SP31 forms a particle size value detection extending step.

On the other hand, at the finish time of the dead time or in the step SP31 of the particle size value detection extending step, if it is judged that the sample value has not exceeded the minimum threshold, the program proceeds to a step SP35. In the step SP35, the particle size range corresponding to a particle detected in the particle size range judging portion 35 is judged from the maximum sample value held in the process of the particle size value detecting step and the particle size value detection extending step, and the threshold of each particle size range set in the threshold setting portion 31, and a pulse is output to a channel of the corresponding particle size range. In the counter portion 4, the number of particles of the particle size range to which the pulse was sent is incremented by one (counting step). The program then returns to the step SP21 for the next counting operation.

By providing such a minimum threshold comparing step, timer start-up step, particle size value detecting step, particle size value detection extending step, and counting step, even particles moving slowly through the flow channel center near a flow channel boundary of the flow channel 12 and exhibiting unstable instability behavior are counted as one particle and as a result, measuring accuracy improves. In particular, by providing the particle size value detecting step and the particle size value detection extending step, even the signal wave forms by a large particle accompanied by an overshoot are counted as one particle and as a result, measuring accuracy improves.

It is to be noted that the present invention is not limited to the embodiments specifically described above and various modifications and applications are possible within the spirit and scope of this invention as set forth in the appended claims. For example, in the embodiments of the present invention, a method for counting the particles in the air is described, but this is only one example. The present invention can also be applied to counting of the particles in an entire fluid including floating particle in a fluid or supercritical phase.

EFFECTS OF THE INVENTION

According to the present invention, even particles moving slowly through a flow channel center near a flow channel boundary of a flow channel formed by the flow of a sample fluid and exhibiting unstable behavior are counted as one particle and as a result, the measuring accuracy improves. Further, even signal wave forms by a large particle accompanied by an overshoot are counted as one particle and as a result, the measuring accuracy improves.

INDUSTRIAL APPLICABILITY

According to the present invention, since one particle is not counted as a plurality of particles, measuring accuracy improves and this contributes to counting operation of the particle in a fluid.

What is claimed is:

1. A particle counting method, comprising:
   a. radiating a fluid sample with a laser light;
   b. causing the laser light to hit a particle in the fluid sample to produce scattered light;
   c. detecting scattered light by a photoelectric conversion element;
   d. defining at least one particle size range;
   e. sequentially comparing a maximum value of the output of the photoelectric conversion element to a threshold preset for each particle size range to thereby count the number of particles for each particle size range;
   f. comparing a sample value of the output of the photoelectric conversion element to a threshold of the minimum particle size;
   g. starting a timer of a predetermined time when the magnitude relation between the sample value and the threshold of the minimum particle size changes in step (f); and
   h. incrementing by one the number of particles of a particle size range corresponding to the maximum sample value among the sample values collected up until the time that the timer is terminated and the sample value becomes smaller than the minimum particle size threshold.

2. A particle counting method, comprising:
   a. radiating a liquid sample by a laser light;
   b. causing the laser light to hit a particle in the liquid sample to produce scattered light;
   c. detecting scattered light by a photoelectric conversion element;
   d. defining at least one particle size range;

e. sequentially comparing a maximum value of the output of the photoelectric conversion element to a threshold preset for each particle size range to thereby count the number of particles for each particle size range;
f. comparing a sample value of the output of the photoelectric conversion element to a threshold of a minimum particle size;
g. sequentially holding the maximum value of the sample value when the sample value becomes larger than the threshold of the minimum particle size for the first time in step (f);
h. starting a timer of a predetermined time and continuing to sequentially hold the maximum value of the sample value when the sample value becomes smaller than the threshold of the minimum particle size for the first time in step (g);
i. restarting the timer and continuing to sequentially hold the maximum value of the sample value when the sample value at the time-out of step (h) is larger than the threshold of step (f); and
j. incrementing by one the number of particles of a particle size range corresponding to the maximum sample value held in step (g), step (h) and step (i) when the sample value at the time-out of the step (h) or step (i) is smaller than the threshold of the minimum particle size.

3. A particle counting method, comprising:
a. radiating an air sample by a laser light;
b. causing the laser light to hit a particle in the air sample to produce scattered light;
c. detecting scattered light by a photoelectric conversion element;
d. defining at least one particle size range;
e. sequentially comparing a maximum value of the output of the photoelectric conversion element to a threshold preset for each particle size range to thereby count the number of particles for each particle size range;
f. comparing a sample value of the output of the photoelectric conversion element to a threshold of the minimum particle size;
g. sequentially holding the maximum value of the sample value when the sample value becomes larger than the threshold of the minimum particle size for the first time in step (f);
h. starting a timer of a predetermined time and continuing to sequentially hold the maximum value of the sample value when the sample value becomes smaller than the threshold of the minimum particle size for the first time in step (g);
i. restarting the timer and continuing to sequentially hold the maximum value of the sample value when the sample value at the time-out of step (h) is larger than the threshold of the minimum particle size; and
j. incrementing by one the number of particles of a particle size range corresponding to the maximum sample value held in step (g), step (h) and step (i) when the sample value at the time-out of the step (h) or step (i) is smaller than the threshold of the minimum particle size.

4. A particle counting method, comprising:
a. radiating an air sample by a laser light;
b. causing the laser light to hit a particle in the air sample to produce scattered light;
c. detecting scattered light by a photoelectric conversion element;
d. defining at least one particle size range;
e. sequentially comparing a maximum value of the output of the photoelectric conversion element to a threshold preset for each particle size range to thereby count the number of particles for each particle size range;
f. comparing a sample value of the output of the photoelectric conversion element to a threshold of the minimum particle size;
g. sequentially holding a maximum value of the sample value when the sample value becomes larger than the threshold of the minimum particle size for the first time in step (f);
h. starting a timer of a predetermined time at the same time as the start of step (g);
i. continuing to sequentially hold the maximum value until when the sample value becomes smaller again than the threshold of the minimum particle size when the sample value at the time-out of step (h) is larger than the threshold of the minimum particle size; and
j. incrementing by one the number of particles of a particle size range corresponding to the maximum sample value held in step (g) and step (i) when the sample value at the time-out of step (g) is smaller than the threshold of the minimum particle size or when the sample value of step (i) is smaller than the threshold of the minimum particle size.

* * * * *